United States Patent
Oberstadt et al.

(10) Patent No.: US 7,507,047 B2
(45) Date of Patent: Mar. 24, 2009

(54) FINGER WIPE CONTAINING A COMPOSITION IN A RUPTURABLE RESERVOIR

(75) Inventors: Jayne Ann Oberstadt, New London, WI (US); Amanda Lee O'Connor, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 463 days.

(21) Appl. No.: 11/020,566

(22) Filed: Dec. 22, 2004

(65) Prior Publication Data
US 2006/0133884 A1 Jun. 22, 2006

(51) Int. Cl.
*A46B 5/04* (2006.01)

(52) U.S. Cl. .............................. 401/7; 401/132; 401/133

(58) Field of Classification Search ................. 401/7, 401/8, 132–135; 604/1–3
See application file for complete search history.

(56) References Cited

U.S. PATENT DOCUMENTS

| | | | |
|---|---|---|---|
| 1,896,941 A | | 2/1933 | Cohen |
| 1,947,720 A | * | 2/1934 | Laub ............................. 401/7 |
| 2,016,951 A | * | 10/1935 | Welker .......................... 401/7 |
| 2,041,262 A | | 5/1936 | Ness |
| 2,599,191 A | | 6/1952 | Meunier |
| 2,646,796 A | | 7/1953 | Scholl |
| 2,673,365 A | | 3/1954 | Moor, Jr. |
| 2,790,982 A | * | 5/1957 | Schneider ..................... 401/7 |
| 2,882,528 A | | 4/1959 | Tassie |
| 2,925,605 A | | 2/1960 | Wheeler |
| 2,966,691 A | | 1/1961 | Cameron |
| 3,070,102 A | | 12/1962 | MacDonald |
| 3,124,824 A | | 3/1964 | Lutz |
| 3,263,681 A | | 8/1966 | Nechtow et al. |
| 3,280,420 A | | 10/1966 | Wanzenberg |
| 3,298,507 A | | 1/1967 | Micciche |
| 3,338,992 A | | 8/1967 | Kinney |
| 3,341,394 A | | 9/1967 | Kinney |
| 3,348,541 A | | 10/1967 | Loebeck |

(Continued)

FOREIGN PATENT DOCUMENTS

DE 19620487 A1 11/1997

(Continued)

OTHER PUBLICATIONS

Medical Textiles, Nov. 1999 "Crimped Bristle Toothbrush". "Nonwoven Removes Stains", "Dental Floss".

(Continued)

*Primary Examiner*—David J Walczak
(74) *Attorney, Agent, or Firm*—Dority & Manning, P.A.

(57) ABSTRACT

A finger wipe that fits onto one or two human fingers. The finger wipe can be used as a substitute for cotton balls, swabs, and/or gauzes, or as an oral cleaning device. The finger wipe includes at least one reservoir that contains a composition. The composition may be a liquid or a solid. For example, in one embodiment, the composition may comprise a cleaning solution, a pharmaceutical, or a skin-conditioning agent. The reservoir is constructed such that the reservoir can be ruptured. For instance, in one embodiment, the reservoir may be ruptured by squeezing two fingers together. In this manner, the composition is released when desired for use in conjunction with the finger wipe.

35 Claims, 8 Drawing Sheets

U.S. PATENT DOCUMENTS

| | | |
|---|---|---|
| 3,368,668 A | 2/1968 | Micciche |
| 3,448,478 A | 6/1969 | Nash et al. |
| 3,485,706 A | 12/1969 | Evans |
| 3,502,763 A | 3/1970 | Hartman |
| 3,542,615 A | 11/1970 | Dobo et al. |
| 3,589,823 A | 6/1971 | Hendrickson |
| 3,675,264 A | 7/1972 | Storandt |
| 3,692,618 A | 9/1972 | Dorschner |
| 3,802,817 A | 4/1974 | Matsuki et al. |
| 3,849,241 A | 11/1974 | Butin et al. |
| 3,853,412 A | 12/1974 | Griffin |
| 3,855,046 A | 12/1974 | Hansen et al. |
| 3,902,509 A | 9/1975 | Tundermann et al. |
| 3,905,113 A | 9/1975 | Jacob |
| 3,952,867 A | 4/1976 | McCord |
| 3,982,298 A | 9/1976 | Ota |
| 4,041,203 A | 8/1977 | Brock et al. |
| 4,084,586 A | 4/1978 | Hettick |
| 4,100,324 A | 7/1978 | Anderson et al. |
| 4,121,312 A | 10/1978 | Penney |
| 4,145,147 A * | 3/1979 | Schuck ............ 401/175 |
| 4,323,534 A | 4/1982 | DesMarais |
| 4,333,979 A | 6/1982 | Sciaraffa et al. |
| 4,335,731 A | 6/1982 | Bora, Jr. |
| 4,340,563 A | 7/1982 | Appel |
| 4,414,970 A | 11/1983 | Berry |
| 4,616,374 A | 10/1986 | Novogrodsky |
| 4,617,694 A | 10/1986 | Bori |
| 4,655,760 A | 4/1987 | Morman et al. |
| 4,657,802 A | 4/1987 | Morman et al. |
| 4,660,228 A | 4/1987 | Ogawa et al. |
| 4,663,220 A | 5/1987 | Wisneski et al. |
| 4,665,901 A | 5/1987 | Spector |
| 4,720,415 A | 1/1988 | Vander Wielen et al. |
| 4,766,029 A | 8/1988 | Brock et al. |
| 4,781,966 A | 11/1988 | Taylor |
| 4,789,699 A | 12/1988 | Kieffer et al. |
| 4,803,117 A | 2/1989 | Daponte |
| 4,818,464 A | 4/1989 | Lau |
| 4,828,556 A | 5/1989 | Braun et al. |
| 4,834,738 A | 5/1989 | Kielpikowski et al. |
| 4,858,245 A | 8/1989 | Sullivan et al. |
| 4,875,247 A | 10/1989 | Berg |
| 4,884,581 A | 12/1989 | Rescigno |
| 4,920,974 A | 5/1990 | Roth et al. |
| 4,926,851 A | 5/1990 | Bulley |
| 4,965,122 A | 10/1990 | Morman |
| D313,317 S | 1/1991 | Brunner et al. |
| 4,981,747 A | 1/1991 | Morman |
| 4,998,978 A | 3/1991 | Varum |
| 5,068,941 A | 12/1991 | Dunn |
| 5,093,422 A | 3/1992 | Himes |
| 5,114,781 A | 5/1992 | Morman |
| 5,116,662 A | 5/1992 | Morman |
| 5,123,113 A | 6/1992 | Smith |
| 5,133,971 A | 7/1992 | Copelan et al. |
| 5,169,706 A | 12/1992 | Collier, IV et al. |
| 5,213,428 A | 5/1993 | Salman |
| 5,226,992 A | 7/1993 | Morman |
| 5,228,433 A | 7/1993 | Rosen |
| 5,280,661 A | 1/1994 | Brown |
| 5,283,924 A | 2/1994 | Kaminski et al. |
| 5,287,584 A | 2/1994 | Skinner |
| 5,304,599 A | 4/1994 | Himes |
| 5,320,531 A | 6/1994 | Delizo-Madamba |
| 5,332,613 A | 7/1994 | Taylor et al. |
| 5,336,545 A | 8/1994 | Morman |
| 5,348,153 A | 9/1994 | Cole |
| 5,356,005 A | 10/1994 | Burrello |
| 5,362,306 A | 11/1994 | McCarver et al. |
| 5,389,202 A | 2/1995 | Everhart et al. |
| 5,393,153 A * | 2/1995 | Bouthillier et al. ......... 401/146 |
| 5,439,487 A | 8/1995 | Stanitzok |
| 5,445,825 A | 8/1995 | Copelan et al. |
| 5,464,294 A * | 11/1995 | Chee et al. ................. 401/269 |
| 5,464,688 A | 11/1995 | Timmons et al. |
| 5,487,201 A | 1/1996 | Hansen et al. |
| 5,502,863 A | 4/1996 | Perkins |
| 5,507,641 A | 4/1996 | Cline |
| 5,541,388 A | 7/1996 | Gadd |
| 5,554,076 A | 9/1996 | Clark |
| 5,591,510 A | 1/1997 | Junker et al. |
| 5,636,405 A | 6/1997 | Stone et al. |
| 5,678,273 A | 10/1997 | Porcelli |
| 5,765,252 A | 6/1998 | Carr |
| 5,766,248 A | 6/1998 | Donovan |
| 5,771,522 A | 6/1998 | Carmody |
| 5,794,774 A | 8/1998 | Porcelli |
| 5,804,021 A | 9/1998 | Abuto et al. |
| 5,911,319 A | 6/1999 | Porcelli et al. |
| 5,931,596 A * | 8/1999 | Javier ........................ 401/268 |
| 5,953,783 A | 9/1999 | Hahn |
| 6,019,773 A | 2/2000 | Denmark |
| 6,065,480 A | 5/2000 | Mader |
| 6,139,514 A | 10/2000 | Benson |
| 6,420,625 B1 | 7/2002 | Jones et al. |
| 6,494,767 B2 | 12/2002 | Fisher |
| 6,508,602 B1 | 1/2003 | Gruenbacher et al. |
| 6,647,549 B2 | 11/2003 | McDevitt et al. |
| 6,721,987 B2 | 4/2004 | McDevitt et al. |
| 6,898,819 B2 | 5/2005 | Tanaka et al. |

FOREIGN PATENT DOCUMENTS

| | | |
|---|---|---|
| EP | 0638277 A1 | 2/1995 |
| EP | 0985364 A2 | 3/2000 |
| EP | 0985364 A3 | 3/2000 |
| EP | 0985364 B1 | 3/2000 |
| FR | 2848535 A1 | 6/2004 |
| GB | 1046146 | 10/1966 |
| GB | 2099305 A | 12/1982 |
| GB | 2227938 A | 8/1990 |
| WO | WO8707122 | 12/1987 |
| WO | WO9203947 | 3/1992 |
| WO | WO9531154 | 11/1995 |

OTHER PUBLICATIONS

Tetra Medical Supply Corp.; Product Information; Jan. 4, 2000; www.tetramed.com/dress.htm.

Spandage; Product Information; Jan. 4, 2000; spandage.com/main.htm.

FootSmark Products; Product Information—Toe Caps & DigiCushions; Jan. 4, 2000; www.footsmart.com.

Abstract of Japanese Patent No. JP06205723.

Abstract of Japanese Patent No. JP06285108.

Abstract of Japanese Patent No. JP10243818, Sep. 14, 1998.

Search Report and Written Opinion for PCT/US2005/033139, Feb. 10, 2006.

* cited by examiner

FINGER WIPE CONTAINING A COMPOSITION IN A RUPTURABLE RESERVOIR

BACKGROUND OF THE INVENTION

Cotton balls, swabs, and gauzes are commonly used for a variety of reasons. For instance, a cotton ball can be used to apply diaper rash ointments, medications, alcohol, oral anesthetics, etc. Moreover, in some cases, a cotton ball can also be utilized to remove various types of materials from a person, such as, for example, facial makeup or may be used to polish or clean various objects. In each of these fields, the cotton ball or swab is typically configured to deliver a particular additive or ingredient to the area of application.

However, in some instances, it may be difficult for a user to apply an additive to a cotton ball, for example, without undesirably spilling some of the additive. Moreover, cotton materials can often be relatively expensive and difficult to process in comparison to other types of materials. As such, a need currently exists for an improved product capable of delivering an additive, such as a medication, to a particular area of application. In particular, a need currently exists for a finger wipe capable of insulating a finger while delivering a particular additive.

In addition, another field in which a device is required to deliver an additive or ingredient is the field of teeth or gum cleaning. Teeth cleaning is regularly required to maintain dental hygiene. Various films and residues, such as plaque, can build up on teeth and gums over a period of time, thereby adversely affecting oral health. In the past, toothbrushes have been utilized to remove such films and residues. Conventional toothbrushes typically have two ends with one end being a handle and the other containing bristles designed to disrupt and remove plaque and other residues from the surfaces being cleaned.

Although conventional toothbrushes are useful in a wide variety of environments, in some circumstances, they are less than desirable. For example, some individuals desire to maintain dental hygiene by brushing their teeth throughout the day. Unfortunately, many daily environments do not provide a setting which fosters or even allows such activity. Moreover, travelers and those working in office environments may not find it convenient to use a toothbrush during the day. For instance, toothbrushes are not generally well suited to be carried by persons on a day-to-day basis because of their bulky shape and the need to have access to a restroom lavatory.

In response to this desire for more frequent dental hygiene and for a cleaning device that can be easily used in public, various portable toothbrushes have been developed. In particular, a number of finger-mounted teeth cleaning devices were developed that could be placed over a finger and wiped over the teeth and gums. These devices are typically small, portable, and disposable.

Examples of oral cleaning devices and finger wipes are disclosed, for instance, in U.S. Pat. No. 6,721,987 to McDevitt, et al. and in U.S. Pat. No. 6,647,549 also to McDevitt, et al., which are incorporated herein by reference.

Although the articles disclosed in the above patents have provided great advances in the art, further improvements are still needed. In particular, a need exists for a disposable finger wipe that is associated with a cleaning or treatment composition. In particular, a need exists for a finger wipe that contains an easily dispensable composition that is incorporated into the structure of the finger wipe. The composition may comprise, for instance, a cleaning solution, a pharmaceutical, and the like.

SUMMARY OF THE INVENTION

Definitions

As used herein, the term "breathable" means pervious to water vapor and gases. In other words, "breathable barriers" and "breathable films" allow water vapor to pass therethrough, but are substantially impervious to liquid water. For example, "breathable" can refer to a film or laminate having water vapor transmission rate (WVTR) of at least about 300 g/m$^2$/24 hours measured using ASTM Standard E96-80, upright cup method, with minor variations as described in the following Test Procedure.

A measure of the breathability of a fabric is the water vapor transmission rate (WVTR) which, for sample materials, is calculated essentially in accordance with ASTM Standard E96-80 with minor variations in test procedure as set forth hereinbelow. Circular samples measuring three inches in diameter are cut from each of the test materials, and tested along with a control, which is a piece of CELGARD 2500 sheet from Celanese Separation Products of Charlotte, N.C. CELGARD 2500 sheet is a microporous polypropylene sheet. Three samples are prepared for each material. The test dish is a No. 60-1 Vapometer pan distributed by Thwing-Albert Instrument Company of Philadelphia, Pa. 100 milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 cm diameter circle having an exposed area of approximately 33.17 square centimeters. The pans are placed in a forced air oven at 100°F (32°C.) for one hour to equilibrate. The oven is a constant temperature oven with external air circulating through it to prevent water vapor accumulation inside. A suitable forced air oven is, for example, a Blue M Power-O-Matic 600 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows: Test WVTR=(grams weight loss over 24 hours)×(315.5 g/m$^2$/24 hours).

The relative humidity within the oven is not specifically controlled. Under predetermined set conditions of 100°F (32°C) and ambient relative humidity, the WVTR for the CELGARD 2500 control has been defined to be 5000 grams per square meter for 24 hours. Accordingly, the control sample was run with each test and the preliminary test values were corrected to set conditions using the following equation: WVTR=(test WVTR/control WVTR)×(5000 g/m$^2$/24 hrs.).

As used herein, the terms "elastic" and "elastomeric" are generally used to refer to materials that, upon application of a force, are stretchable to a stretched, biased length which is at least about 125%, or one and a third times, its relaxed, unstretched length, and which will retract at least about 50% of its elongation upon release of the stretching, biasing force.

As used herein, "meltblown fibers" refers to fibers formed by extruding a molten thermoplastic material through a plurality of fine, usually circular, die capillaries as molten threads or filaments into converging high velocity, usually hot, gas (e.g. air) streams which attenuate the filaments of thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al. Meltblown fibers are microfibers which may be continuous or discontinuous, are generally smaller than 10 microns in average diameter, and are generally tacky when deposited on a collecting surface.

As used herein, a "liquid impermeable layer" refers to any material that is relatively impermeable to the transmission of fluids, i.e. a fabric having a liquid impermeable layer can have a blood strikethrough ratio of 1.0 or less according to ASTM test method 22.

As used herein, the term "neck-bonded" refers to an elastic member being bonded to a non-elastic member while the non-elastic member is extended in the machine direction creating a necked material. "Neck-bonded laminate" refers to a composite material having at least two layers in which one layer is a necked, non-elastic layer and the other layer is an elastic layer thereby creating a material that is elastic in the cross direction. Examples of neck-bonded laminates are such as those described in U.S. Pat. Nos. 5,226,992; 4,981,747; 4,965,122; and 5,336,545, all to Morman, all of which are incorporated herein by reference thereto.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel, et al.; U.S. Pat. No. 3,692,618 to Dorschner, et al.; U.S. Pat. No. 3,802,817 to Matsuki, et al.; U.S. Pat. No. 3,338,992 to Kinney; U.S. Pat. No. 3,341,394 to Kinney; U.S. Pat. No. 3,502,763 to Hartman: and U.S. Pat. No. 3,542,615 to Dobo, et al. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "stretch-bonded" refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25 percent of its relaxed length. Such a multilayer composite elastic material may be stretched until the nonelastic layer is fully extended. One type of stretch-bonded laminate is disclosed, for example, in U.S. Pat. No. 4,720,415 to Vander Wielen, et al., which is incorporated herein by reference. Other composite elastic materials are described and disclosed in U.S. Pat. No. 4,789,699 to Kieffer, et al.; U.S. Pat. No. 4,781,966 to Taylor; U.S. Pat. No. 4,657,802 to Morman; and U.S. Pat. No. 4,655,760 to Morman. et al., all of which are incorporated herein by reference thereto.

As used herein, the term "texturized" refers to a base web having projections from a surface of the web in the Z-direction. The projections can have a length, for instance, from about 0.1mm to about 25mm, particularly from about 0.1mm to about 5mm, and more particularly from about 0.1mm to about 3mm. The projections can take on many forms and can be, for instance, bristles, tufts, loop structures such as the loops used in hook and loop attachment structures, and the like.

As used herein, the term "coform web" refers to a material produced by combining separate polymer and additive streams into a single deposition stream in forming a nonwoven web. Such a process is taught, for example, by U.S. Pat. No. 4,100,324 to Anderson, et al. which is hereby incorporated by reference.

Summary

The present disclosure is generally directed to a finger wipe that can fit over a finger. For instance, in one embodiment, the finger wipe can be used as a dental wipe to clean the mouth of a user or of an animal, such as a pet. According to the present invention, a composition, such as a liquid or solid composition, is incorporated into the structure of the finger wipe for providing various benefits and advantages during use of the wipe. The composition may be, for instance, a cleaning solution, a pharmaceutical, a therapeutic substance, and the like. In one embodiment, for instance, the composition may be contained in a reservoir that is ruptured during use of the product.

In one embodiment, for example, the present invention is directed to a finger wipe comprising a hollow member having an open end for the insertion of a finger. The hollow member includes a liquid impermeable layer positioned to prevent liquids from contacting a finger contained in the hollow member. The liquid impermeable layer, for instance, may comprise a film, such as a breathable film, that forms an interior surface of the hollow member.

The hollow member further includes a cover layer that has at least one liquid permeable portion. The cover layer, for instance, may be a nonwoven material and can be liquid permeable in one section or over the entire surface of the cover layer. The cover layer, for instance, may comprise a spunbonded web, a meltblown web, a spunbonded/meltblown/spunbonded laminate, a spunbonded/meltblown laminate, a bonded carded web, a coform web, and combinations thereof. In order to increase the liquid permeability of the cover layer, the cover layer may be perforated.

In accordance with the present invention, the hollow member further includes a reservoir positioned in between the liquid impermeable layer and the cover layer. The reservoir is configured to be ruptured by a user. A composition is contained in the reservoir. When the reservoir is ruptured by a user, the composition is released from the reservoir and migrates through the liquid permeable portion of the cover layer. In this manner, the composition remains protected and stored until the finger wipe is placed into use.

The reservoir positioned in between the cover layer and the liquid impermeable layer may be made from various materials. In one embodiment, for instance, the reservoir is made from one or more films. The reservoir may be attached to the liquid impermeable layer. In fact, in one embodiment, the liquid impermeable layer may form a surface of the reservoir.

The composition contained within the reservoir may vary depending upon the particular application. In general, any suitable composition may be contained in the reservoir, such as a liquid or a solid. The composition may be, for instance, a cleaning solution or a pharmaceutical. For instance, in various embodiments, the composition may comprise a tooth cleaner, a furniture polish, a window cleaner, a mite, tick or flea control additive, a makeup removal composition, and the like.

As stated above, the reservoir is configured to be ruptured by the user. For example, in one embodiment, the reservoir may be constructed so as to rupture when squeezed between a user's pair of opposing fingers. In an alternative embodiment, the finger wipe may be packaged with a lancing tool that is used to lance or break open the reservoir.

The finger wipe can include one or more elastic components in order to provide the wipe with form-fitting properties. For example, in one embodiment, the finger wipe may include a first panel attached to a second panel. The first panel may comprise an elastic member, such as an elastic nonwoven material. For instance, the first panel may be made from a neck-bonded material or a stretch-bonded material and may be configured to be positioned adjacent the back of a person's finger.

The second panel, on the other hand, may be made from the liquid impermeable layer, the cover layer, and the reservoir. The first panel and the second panel may be attached together using any suitable method. In one particular embodiment, the first panel may be thermally or ultrasonically bonded with the second panel to form a seam.

In one embodiment, the first panel and the second panel may include an overlapping portion that extends beyond the seam. The overlapping portion which forms a flange around the product may have a width of from about 1 mil to about 0.75 inches. For instance, the width of the overlapping portion may be from about 3 mils to about 0.5 inches, such as from about 0.1 inches to about 0.3 inches. The overlapping portion or flange may be periodically severed along the width of the overlapping portion. In this manner, the overlapping portion enhances the ability of the finger wipe to clean adjacent surfaces.

In addition to or instead of the above-described overlapping portion, the finger wipe may also include a texturized surface. The texturized surface may contain looped bristles or a point unbonded material that may be used to scrub an adjacent surface.

In an alternative embodiment of the present invention, the finger wipe includes a hollow member having an open end for the insertion of one or more fingers. If desired, the hollow member may also include a closed end opposite the open end. The hollow member includes a liquid impermeable layer as described above and a fibrous material located over at least a portion of the liquid impermeable layer. The fibrous material may be impregnated with a composition, such as a liquid or solid material. In this embodiment, the finger wipe further includes a release layer covering the fibrous material and forming an exterior surface of the finger wipe. The release layer is configured to be peeled away by a user for exposing the fibrous material.

For example, the release layer may comprise a film that is adhered to the finger wipe at locations surrounding the fibrous material. Thus, the release layer serves to encapsulate the composition that is impregnated into the fibrous material.

In one embodiment, the fibrous material may be positioned on a fingertip portion of the finger wipe. The finger wipe may further include a nonwoven material covering other portions of the wipe.

It should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91% to 99.999%.

Various features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth in the specification, which makes reference to the appended drawings, in which.

Figure 1:
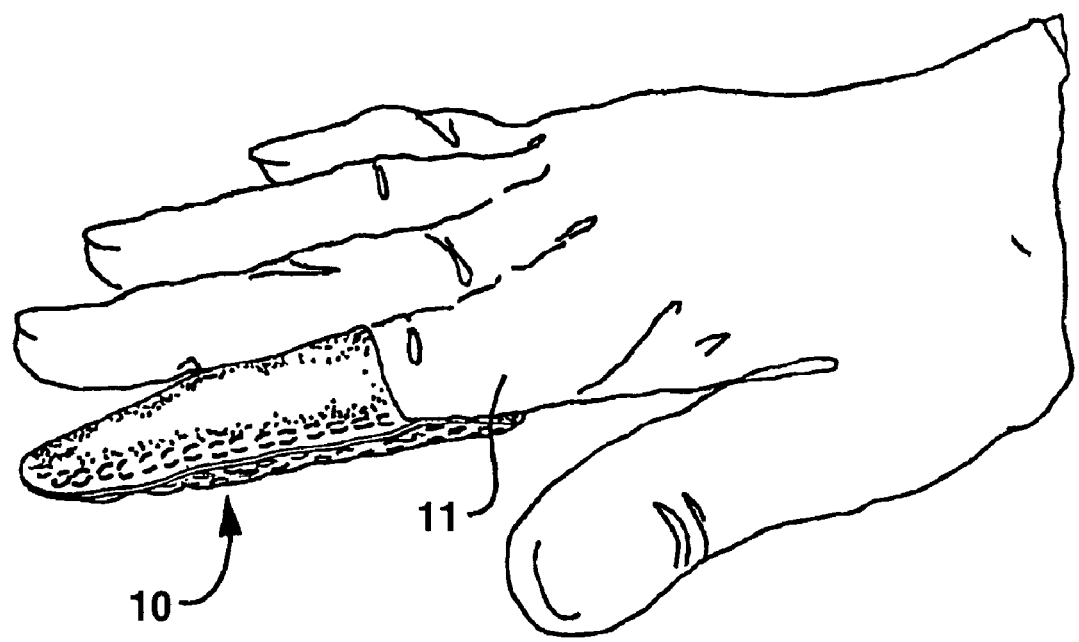
FIG. 1 is a perspective view of a finger wipe on a finger according to one embodiment of the present invention.
Figure 2:
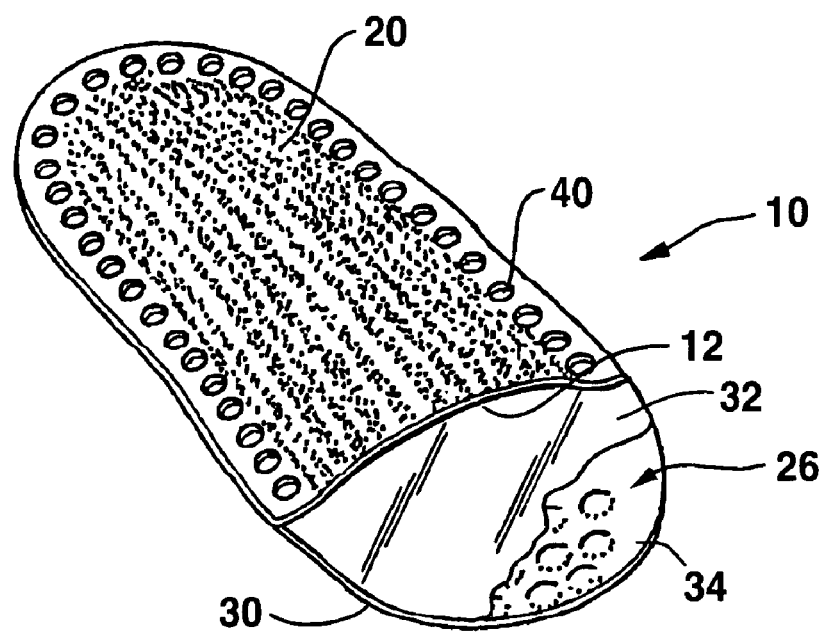
FIG. 2 is a perspective view of a two-sided finger wipe according to one embodiment of the present invention.
Figure 3:
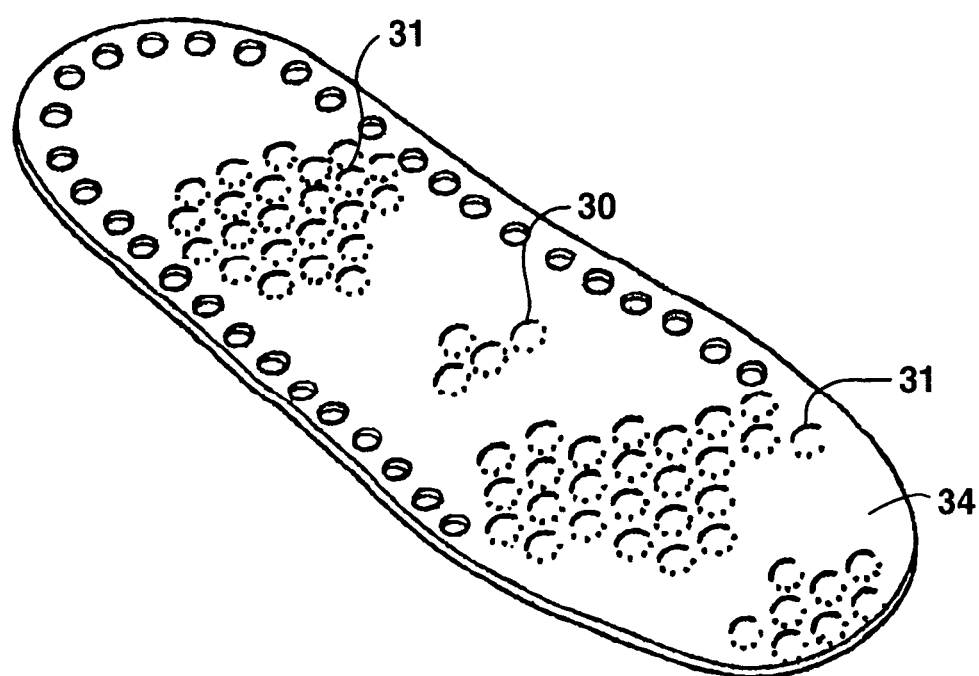
FIG. 3 is a perspective view of a bottom section of a two-sided finger wipe according to one embodiment of the present invention.

Repeat use of reference characters in the present specification and drawings is intended to represent the same or analogous features or elements of the invention.

DETAILED DESCRIPTION

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description.

In general, the present invention is directed to a finger wipe that can be used in various applications. For example, in one embodiment, the finger wipe is a dental wipe that can be more easily used during the day than toothbrushes. In particular, the present invention is directed to a dental wipe that can fit onto a human finger so that the teeth or gums of a person or animal can be cleaned by simply contacting the wipe therewith. For instance, the dental wipe of the present invention can be used by an individual to clean one's teeth or to clean the teeth of someone else, such as an infant, an elderly person, or a pet. Further, the dental wipe is particularly well suited for use by small children learning how to clean their teeth.

Besides being used to clean the teeth or gums of the user, the finger wipe of the present invention can also be used in other applications. For instance, the finger wipe may be used to clean or treat other parts of the body such as the eyes, the ears, the nose, and the like. The finger wipe, for instance, may be used to clean the ears and nose of a person or to apply a medicine to the above areas should diagnostic testing confirm an infection. The finger wipe may also be used to apply mascara and other cosmetics to the face or to wipe away and remove cosmetics.

In still other embodiments, the finger wipe can be used to clean various utensils, objects or surfaces and/or to polish the various items. For example, in one embodiment, the finger wipe can be used to polish silver.

In accordance with the present invention, the finger wipe includes a reservoir, such as an encapsulated area, for containing any number of substances or compositions that are configured to be released upon use of the finger wipe. For example, the finger wipe may contain a bladder made from, for instance, film materials that is configured to be ruptured by a user when a sufficient amount of pressure is applied to the bladder. The bladder may contain, for instance, any suitable liquid or powder composition. The bladder may contain, for example, a cleaning solution such as a tooth cleaner, a pharmaceutical, a skin conditioning composition, and the like.

In an alternative embodiment, instead of containing a rupturable bladder, the finger wipe may include a fibrous material that is impregnated with a composition. The fibrous material may be located on an exterior surface of the finger wipe and may be covered by a release layer. The release layer, for instance, may include a tab for allowing a user to remove the release layer and expose the impregnated fibrous material during use of the finger wipe.

The finger wipe generally is a disposable, absorbent or non-absorbent article which fits on one or more fingers. A liquid impermeable layer may be incorporated into the finger wipe to prevent any fluids from contacting the wearer's fingers.

The finger wipes can be made from numerous different types of materials. For instance, in one embodiment, nonwoven webs made from synthetic and/or pulp fibers may be used. For example, when used as an oral cleaning device, the finger wipe typically includes a texturized surface adapted to scrub or brush the teeth or gums of a user. Further, the finger wipe can also include an elastic component for providing the wipe with form-fitting properties.

A finger wipe of the present invention can generally be formed in a variety of ways. For instance, in one embodiment, the finger wipe can be formed as a unitary structure from a particular base web or laminate material. Moreover, in another embodiment of the present invention, the finger wipe can be formed from two or more sections or panels. Each section can be identical or different, depending on the desired characteristics of the finger wipe. For example, in one embodiment, the finger wipe is formed from two sections, wherein one section is formed from a textured nonwoven material and the other section is formed from an elastomeric nonwoven material.

Referring to FIGS. 1-6 and 9-11, various embodiments of finger wipes made in accordance with the present invention are depicted. Referring particularly to FIGS. 1-4, one embodiment of a finger wipe 10 made in accordance with the present invention is shown. As illustrated in FIG. 1, the finger wipe 10 is configured to be placed over a finger 11. In FIG. 1, for instance, the finger wipe 10 is placed over a single finger 11. It should be understood, however, that the finger wipe may be constructed to fit over multiple fingers if desired.

In the embodiments shown in FIGS. 1-4, instead of a unitary structure, the finger wipe 10 is made from a first panel 20 and a second panel 30. Generally, one panel of the finger wipe 10 can be bonded or attached to the other panel in a finger-shaped pattern by any manner known in the art, such as by adhesive, thermal (including ultrasonic), or mechanical bonding, so that the connection of the panels can form a pocket 12 for the insertion of a finger. In the illustrated embodiment for example, the first panel 20 is attached in a finger-shaped pattern to the second panel 30 at their respective outer edges via the seams 40 to form a finger wipe 10 having a pocket 12. Once each panel is bonded or attached at the seams 40, the materials forming each of the panels 20 and 30 can then be cut adjacent to the seams such that the finger-shaped wipe 10 is formed.

As shown, the second panel 30 can, in some embodiments, have a length greater than the first panel 20 such that second panel 30 includes a portion (or pull-on tab) 26 that extends beyond the edge of the first panel 20. By extending beyond the first panel 20, the portion 26 can facilitate placement of a finger wipe 10 over a finger. In particular, a user can conveniently grab the portion 26 to place the finger wipe 10 over a finger. Besides the second panel 30, a pull-on tab can be positioned on any suitable portion of the finger wipe. For instance, the pull-on tab can be located on the first panel also.

Further, in another embodiment, the pull-on tab can also be provided in the middle portion of the finger wipe 10 such that a user can pull the tab in a direction perpendicular to the lengthwise direction of a flattened finger wipe. As a result, the tab can facilitate the insertion of a finger into the wipe 10 by "spreading out" the wipe in an upwardly direction as a finger is inserted therein.

For many applications, an elastic component or member may be incorporated into the finger wipe 10 for providing the finger wipe with form-fitting properties. In the embodiment illustrated in FIGS. 1-4, for instance, the first panel 20 may be made from an elastic material. For example, in one embodiment, the first panel 20 may be constructed from nonwoven webs containing an elastic component referred to herein as an "elastic nonwoven". An elastic nonwoven is a nonwoven material having non-elastic and elastic components or having purely elastic components. It should be understood, however, that instead of having a panel made from elastic material as shown in FIGS. 1-4, in alternative embodiments, an elastic component, such as a film, strands, nonwoven webs, or elastic filaments may otherwise be incorporated into the structure for providing the desired degree of elasticity. For instance, in other embodiments, the elastic component may be incorporated into the second panel 30 or may be incorporated into both panels.

Figure 4:
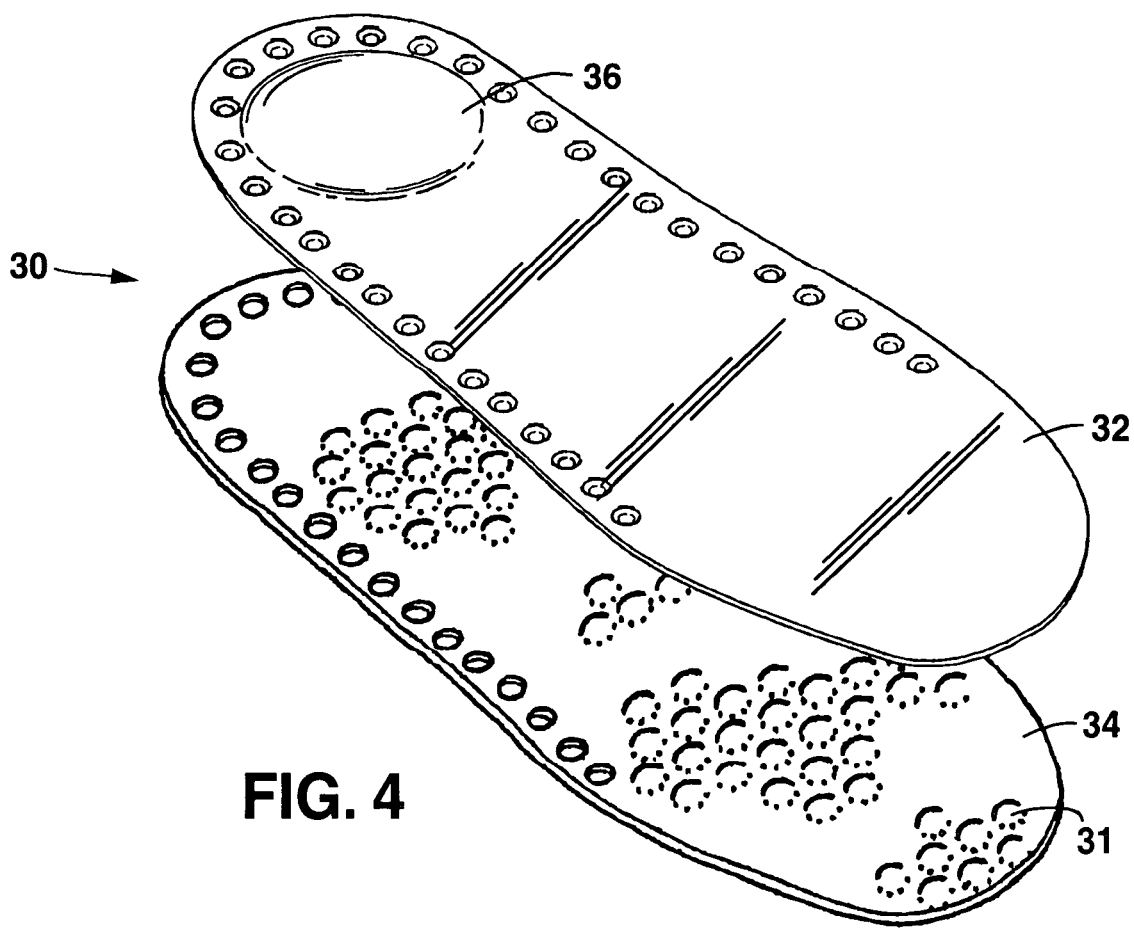
FIG. 4 is an exploded view of one panel of the finger wipe illustrated in FIG. 1.

The second panel 30 of the finger wipe 10 contains various layers as particularly shown in FIG. 4. In particular, the second panel 30 may include a liquid impermeable layer 32, a cover layer 34, and a reservoir 36 positioned in between the liquid impermeable layer 32 and the cover layer 34. The reservoir 36 contains a composition and is configured to be ruptured or punctured by a user for releasing the composition when desired.

In accordance with the present invention, the liquid impermeable layer 32 is for preventing liquids from contacting a user's finger during the use of the finger wipe 10. In general, the liquid impermeable layer 32 can be made from any suitable material such as a film. In one embodiment, as described in greater detail below, the liquid impermeable layer may be breathable.

As shown in FIG. 4, the reservoir 36, in this embodiment, is positioned on the liquid impermeable layer 32 generally in a fingertip area of the finger wipe 10. The reservoir 36 may be constructed of any suitable material capable of holding or containing a composition and then releasing the composition when desired by a user. The reservoir 36, for instance, may be formed from any suitable film material. For instance, in one embodiment, the reservoir 36 may comprise a separate bladder formed from a film that is attached to the liquid impermeable layer 32. In an alternative embodiment, the reservoir 36 may be formed from a film material that is bonded or attached to the liquid impermeable layer 32. In this embodiment, the liquid impermeable layer 32 forms the bottom of the reservoir 36. The film material may be bonded to the liquid impermeable layer 32 by any suitable means, such as by being thermally or ultrasonically bonded to the liquid impermeable layer.

The reservoir 36 may be constructed so as to rupture or be punctured using any suitable technique. For instance, in one embodiment, the reservoir 36 may be configured to rupture when the reservoir is squeezed between two opposing fingers. In another embodiment, the finger wipe 10 may be packaged with a lancing tool that is used to lance or puncture the reservoir 36 when desired.

Suitable film materials that may be used to construct the reservoir 36 include, but are not limited to, polyolefin films such as polypropylene films and polyethylene films, polyester films, polyvinyl chloride films, laminates thereof, and the like. The reservoir 36 may have a size so as to only cover the fingertip area of the finger wipe 10 as shown in FIG. 4 or may have a much larger size covering a greater area of the finger wipe.

In general, any suitable composition may be contained in the reservoir 36 depending upon the desired end use of the finger wipe. The composition contained in the reservoir 36, for instance, may be a fluid or a powder. The composition, for instance, may be an absorbent material, a cleaning solution, a pharmaceutical such as a treatment solution, or a cleansing solution. If the finger wipe 10 is to be used to clean or brush teeth, for instance, the composition contained in the reservoir 36 may comprise a tooth cleaning solution. In other embodiments, the composition contained in the reservoir 36 may comprise a cleaning or polishing solution for cleaning or polishing furniture or eyeglasses, may comprise a mite, tick or flea control agent if the finger wipe 10 is to be used on an animal, or may comprise an agent to prevent against ear infections and/or to treat ear infections or nose and sinus infections.

When the finger wipe 10 is used to remove makeup, the composition contained in the reservoir may be a cleaning solution to facilitate the removal of the makeup or mascara. In still other embodiments, a skin-conditioning agent may be contained in the reservoir, such as a moisturizer, an antimicrobial agent, and the like. Examples of still further compositions that may be contained in the reservoir include diaper rash ointments, alcohols, oral anesthetics, saline solutions, fragrances, therapeutic oils, antibiotics, flavorants, and the like.

When the finger wipe 10 is used to brush or treat the teeth of a human or an animal, the composition may comprise a cationic substance that can help clean teeth and/or the gums. Cationic substances have a strong attraction for negatively charged bacteria and deleterious acidic byproducts that may accumulate in plaque. The cationic substance, for instance, may comprise chitosan or chitosan salts. Other dental agents include, but are not limited to, alginates, soluble calcium salts, phosphates, fluorides such as sodium fluoride or stannous fluoride, or various whitening agents such as peroxides. The composition, in this embodiment, may also include a breath freshening agent such as a mouthwash.

As shown in FIG. 4, in addition to the liquid impermeable layer 32 and the reservoir 36, the second panel 30 of the finger wipe 10 may optionally include a cover layer 34. The cover layer 34 can be an absorbent material as shown in the figures or, alternatively, can comprise a non-absorbent material. The cover layer 34 includes at least one liquid permeable portion that is positioned over the reservoir 36 for allowing compositions to migrate to the surface from the reservoir once the reservoir is ruptured. In one embodiment, for instance, the entire cover layer may be liquid permeable. In other embodiments, however, the portion of the cover layer covering the reservoir 36 may have a greater liquid permeability than the remainder of the cover layer. For example, the cover layer may be apertured in the area covering the reservoir 36. The size of the apertures may vary depending upon the particular application. In one embodiment, for instance, the cover layer 34 may be perforated. Alternatively, the cover layer 34 may be needle punched for increasing the liquid permeable characteristics of the layer. In still another embodiment, the portion of the cover layer 34 that covers the reservoir 36 may have a lower basis weight than the remainder of the cover layer. For instance, portions of the cover layer 34 not covering the reservoir 36 may have an increased density and may contain liquid absorbent materials, such as a superabsorbent.

Figure 5:
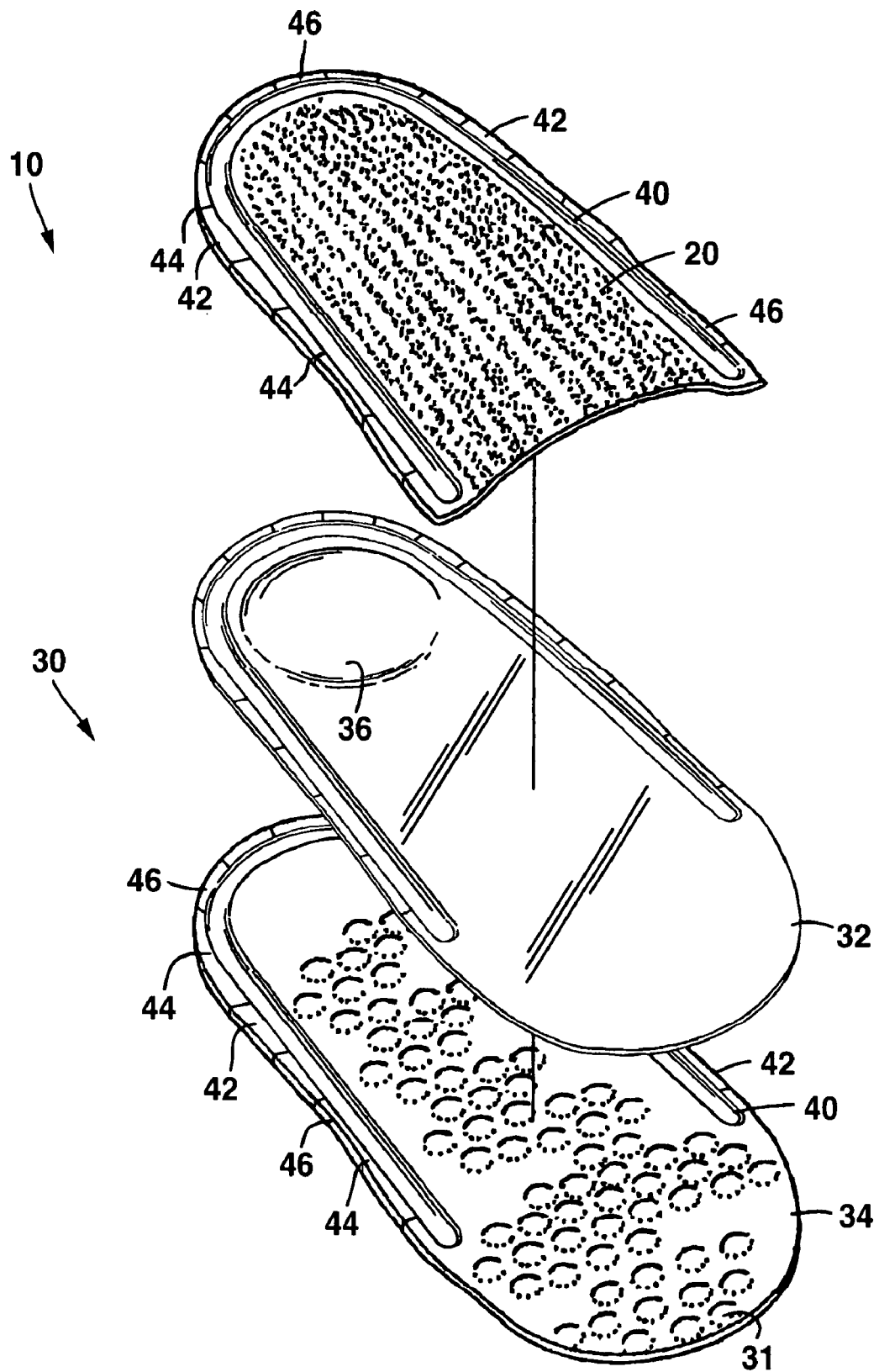
FIG. 5 is an exploded view of another embodiment of a finger wipe made according to the present invention.

Referring to FIG. 5, another embodiment of a finger wipe generally 10 may in accordance with the present invention is shown. Like reference numerals have been used to indicate similar elements. As shown in FIG. 5, the finger wipe 10 includes a first panel 20 attached to a second panel 30. The second panel 30 is shown in an exploded view to better illustrate the different layers. In particular, the second panel 30 includes a liquid impermeable layer 32, a cover layer 34, and a reservoir 36 positioned in between the liquid impermeable layer 32 and the cover layer 34. In this embodiment, the first panel 20 is bonded with the second panel 30 to form a continuous seam 40. The seam 40 may be formed, for instance, by thermally or ultrasonically bonding the two panels together.

As illustrated in FIG. 5, the first panel 20 forms an overlapping portion 42 with the second panel 30. The overlapping portion 42 extends beyond the seam 40. As also shown, the overlapping portion 42 is periodically severed along the width of the overlapping portion. In particular, the finger wipe includes slits 44 positioned around the perimeter of the finger wipe 10. In this manner, flaps 46 are formed. The flaps may serve to enhance the cleaning ability of the finger wipe by increasing surface area and contact points.

The width of the overlapping portion 42 may vary depending upon the particular application. In general, for instance, the overlapping portion may have a width of up to about 0.5 inches, such as from about 0.1 inches to about 0.4 inches. In one embodiment, for instance, the flaps 46 may have a width of from about 0.15 inches to about 0.25 inches.

Figure 6:
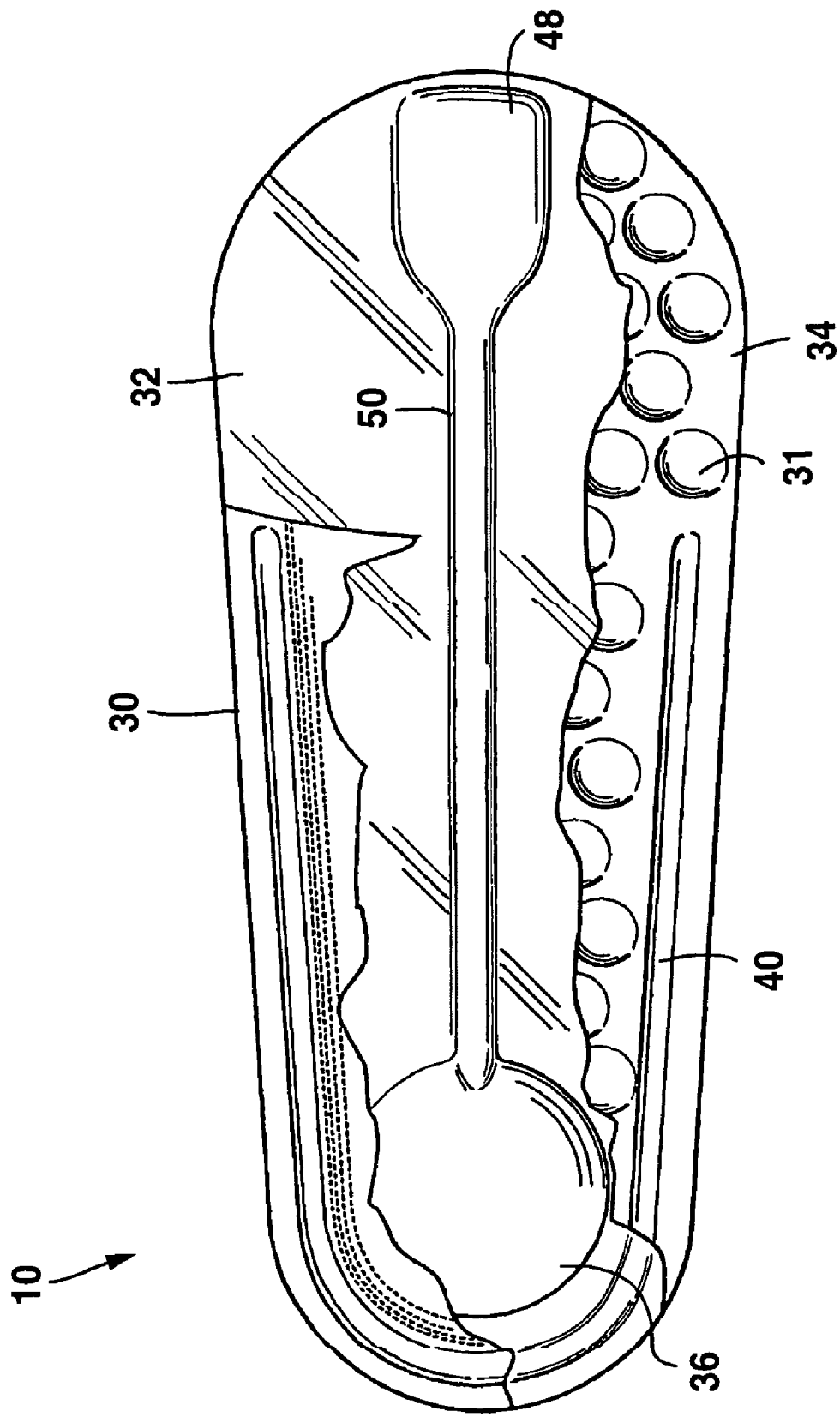
FIG. 6 is a top view with cutaway portions of another embodiment of a finger wipe made in accordance with the present invention.

Referring to FIG. 6, another embodiment of a finger wipe 10 generally made in accordance with the present invention is shown. Again, common reference numerals have been used to indicate similar elements. FIG. 6 is a plan view of the second panel 30 of the finger wipe 10 with cutaway portions. As shown, the finger wipe includes a liquid impermeable layer 32 configured to be placed adjacent to a user's finger. A cover layer 34 is present that overlaps the liquid impermeable layer 32. In accordance with the present invention, the finger wipe 10 further includes a first reservoir 36.

In the embodiment illustrated in FIG. 6, the finger wipe 10 further includes a second reservoir 48. The second reservoir 48 is in fluid communication with the first reservoir 36 via a channel 50. The second reservoir 48 is for supplying further amounts of the composition to the first reservoir 36 after the first reservoir 36 is ruptured.

In one embodiment, for example, the second reservoir 48 may contain additional amounts of the composition that may be fed to the first reservoir 36 by squeezing the second reservoir 48. In an alternative embodiment, greater amounts of the composition may be introduced into the second reservoir 48 for flowing to the first reservoir 36. For instance, a syringe may be used in order to introduce further amounts of the composition into the second reservoir 48.

In the embodiment illustrated in FIG. 6, the second reservoir 48 is contained within the second panel 30 of the finger wipe 10. In an alternative embodiment, however, the second reservoir 48 may extend beyond the length of the second panel 30. For instance, in one embodiment, the second reservoir 48 may be configured to be placed in the palm of one's hand while wearing the finger wipe 10 on one's finger. When placed in the palm of the hand, the second reservoir may be squeezed by the person's hand in order to flow further amounts of the composition into the first reservoir 36.

Examples of materials that may be used to construct the finger wipe 10 as shown in FIGS. 1-6 will now be discussed in greater detail.

Cover Layer

As described above, the cover layer 34 as shown in FIGS. 1-6 is optional. When present, the cover layer may comprise a liquid absorbent material or a non-absorbent material. When comprising a liquid absorbent material, the cover layer 34 may comprise any suitable fabric material, such as a woven fabric, a nonwoven fabric, or a knitted fabric.

In one embodiment, the cover layer 34 comprises a spunbond web, a coform web, a tissue web, a meltblown web, a bonded carded web, and laminates thereof. A nonwoven material can be made from various fibers, such as synthetic or natural fibers. For instance, in one embodiment, synthetic fibers, such as fibers made from thermoplastic polymers, can be used to construct the cover layer of the present invention. For example, suitable fibers could include melt-spun filaments, staple fibers, melt-spun multi-component filaments, and the like. These synthetic fibers or filaments used in making the nonwoven material may have any suitable morphology and may include hollow or solid, straight or crimped, single component, conjugate or biconstituent fibers or filaments, and blends or mixtures of such fibers and/or filaments, as are well known in the art.

The synthetic fibers used in the present invention may be formed from a variety of thermoplastic polymers where the term "thermoplastic polymer" refers to a long chain polymer that repeatedly softens when exposed to heat and substantially returns to its original state when cooled to ambient temperature. As used herein, the term "polymer" generally includes, but is not limited to, homopolymers, copolymers, such as for example, block, graft, random, and alternating copolymers, terpolymers, etc., and blends and modifications thereof.

Exemplary thermoplastics include, without limitation, poly(vinyl) chlorides, polyesters, polyamides, polyfluorocarbons, polyolefins, polyurethanes, polystyrenes, poly(vinyl) alcohols, caprolactams, and copolymers of the foregoing, and elastomeric polymers such as elastic polyolefins, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene), A-B-A-B tetrablock copolymers and the like.

Many polyolefins are available for fiber production, for example polyethylenes such as Dow Chemical's PE XU 61800.41 linear low-density polyethylene ("LLDPE") and 25355 and 12350 high-density polyethylene ("HDPE") are such suitable polymers. Fiber-forming polypropylenes include Exxon Chemical Company's Escorene® PD 3445 polypropylene and Montell Chemical Co.'s PF-304 and PF-015. Many other polyolefins are commercially available and include polybutylenes and others.

Synthetic fibers added to the nonwoven web can also include staple fibers which can be added to increase the strength, bulk, softness and smoothness of the base sheet. Staple fibers can include, for instance, various polyolefin fibers, polyester fibers, nylon fibers, polyvinyl acetate fibers, cotton fibers, rayon fibers, non-woody plant fibers, and mixtures thereof.

Besides or in addition to synthetic fibers, pulp fibers can also be used to construct the cover layer. The pulp fibers used in forming the cover layer may be soft wood fibers having an average fiber length of greater than 1 mm, and particularly from about 2 to 5 mm based on a length weighted average. Such fibers can include northern softwood kraft fibers, redwood fibers, and pine fibers. Secondary fibers obtained from recycled materials may also be used. In addition, hardwood pulp fibers, such as eucalyptus fibers, or thermomechanical pulp can also be utilized in the present invention.

In some embodiments of the present invention, the cover layer can include a hydraulically entangled web (or hydroentangled). Hydroentangled webs, which are also known as spunlace webs, refer to webs that have been subjected to columnar jets of a fluid that cause the fibers in the web to entangle. For example, in one embodiment, the cover layer can comprise HYDROKNIT®, a nonwoven composite fabric that contains 70% by weight pulp fibers that are hydraulically entangled into a continuous filament material. HYDROKNIT® material is commercially available from Kimberly-Clark Corporation of Neenah, Wis. Hydraulic entangling may be accomplished utilizing conventional hydraulic entangling equipment such as may be found in, for example, U.S. Pat. Nos. 3,485,706 to Evans or 5,389,202 to Everhart, et al., the disclosures of which are hereby incorporated by reference.

In one embodiment, the cover layer may comprise a laminate containing two or more webs. For instance, the cover layer may comprise a spunbonded/meltblown/spunbonded laminate, a spunbonded/meltblown laminate and the like.

For nonwoven webs containing substantial amounts of synthetic fibers, the webs may be bonded or otherwise consolidated in order to improve the strength of the web. Various methods may be utilized in bonding webs of the present invention. Such methods include through air bonding and thermal point bonding as described in U.S. Pat. No. 3,855,046 to Hansen, et al. which is incorporated herein by reference. In addition, other conventional means of bonding, such as oven bonding, ultrasonic bonding, hydroentangling, or combinations of such techniques, may be utilized in certain instances.

In one embodiment, thermal point bonding is used which bonds the fibers together according to a pattern. In general, the bonding areas for thermal point bonding, whether pattern unbonded or pattern bonded fabrics, can be in the range of 50% total bond area or less. More specifically, the bond areas of the present inventive webs can be in the range of from about 40% to about 10% total bond area.

When the finger wipe of the present invention is used to scrub adjacent surfaces or is to be used in dental applications, in some embodiments, the cover layer may include a texturized surface such as the surface illustrated in the embodiments shown in FIGS. 1-6. When used in dental applications, for instance, the texturized surface can facilitate removal of residue and film from the teeth and gums.

The manner in which a texturized surface is formed on a nonwoven web for use in the present invention can vary depending upon the particular application of the desired result. In the embodiment shown in FIGS. 1-6, the cover layer 34 is made from a nonwoven web that has been thermally point unbonded to form a plurality of tufts 31. As used herein, a substrate that has been "thermally point unbonded" refers to a substrate that includes raised unbonded areas or lightly bonded areas that are surrounded by bonded regions. For example, as shown in the figures, the tufts 31 are the unbonded or lightly bonded areas that form raised projections off the surface of the nonwoven web to provide the necessary texture.

Figure 7:
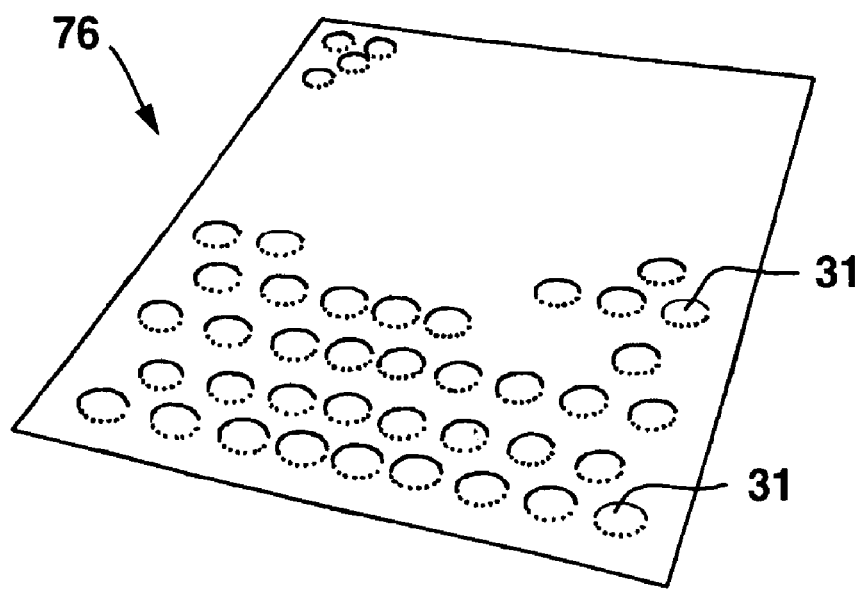
FIG. 7 is a perspective view of a texturized material for use in the present invention.
Figure 8:
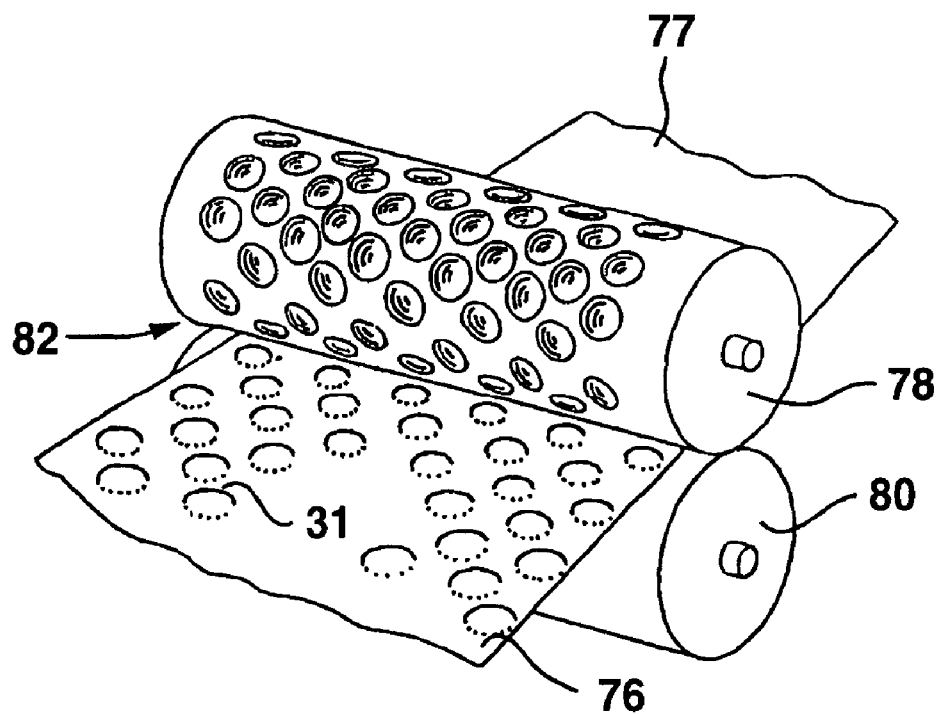
FIG. 8 is a perspective view of one embodiment of a process for producing the material illustrated in FIG. 7.
Figure 9:
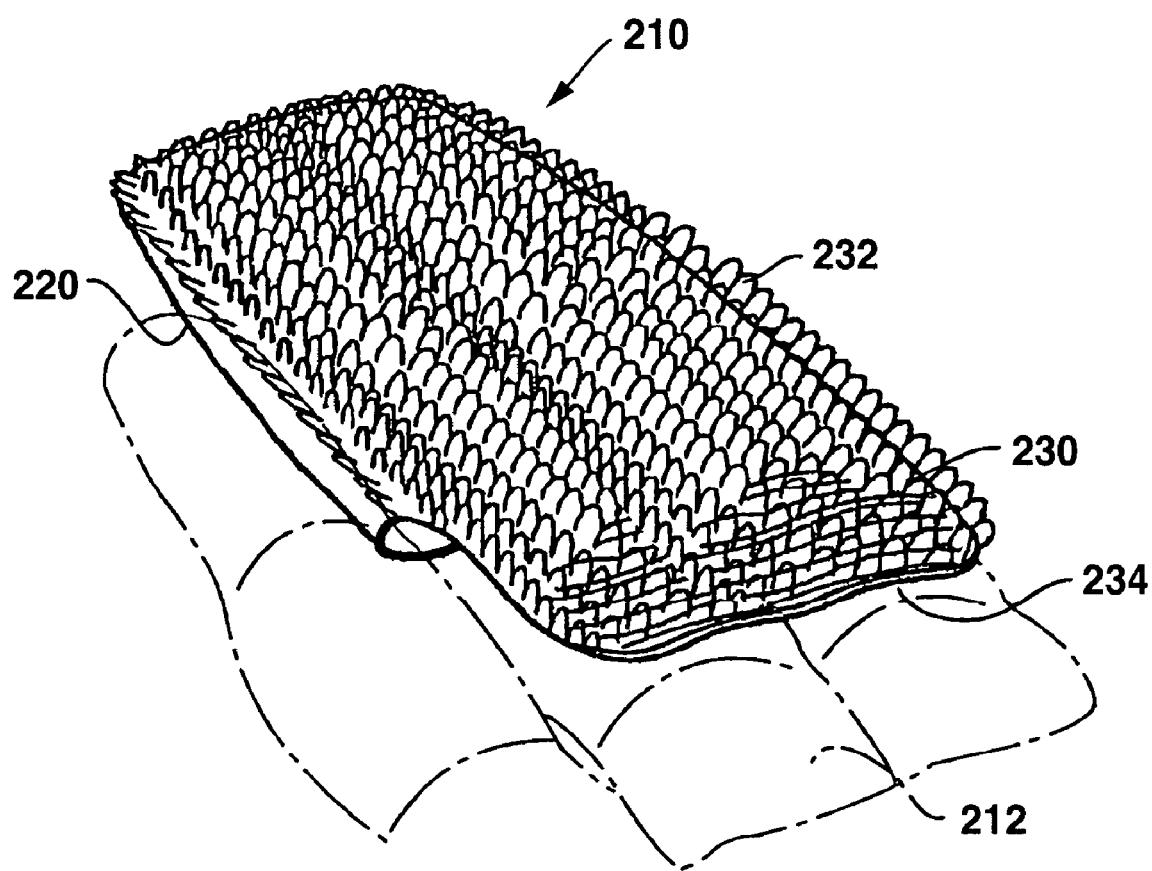
FIG. 9 is still another embodiment of a finger wipe made according to the present invention.

Referring to FIGS. 7 and 8, one embodiment of a process for producing a point unbonded material 76 is illustrated. As shown, a nonwoven substrate 77 is fed into a nip generally 82 formed between a first patterned roll 78 and a second smooth roll 80. Once the substrate is fed through the nip 82, the tufts 31 are formed. As shown, the tufts 31 are surrounded by bonded, compressed regions.

The substrate 77 used to produce the point unbonded material 76 can vary depending upon the particular application. For instance, the substrate 77 can be a single layer or can include multiple layers of material. For most applications, the total basis weight of the substrate 77 should be at least 3 osy, and particularly from about 3 osy to about 9 osy. Higher basis weights are needed in order to produce tufts 31 with an appropriate height.

For most applications, the substrate 77 should also include at least one nonwoven layer that has a high bulk to mass ratio. Examples of materials having high bulk include through air bonded nonwoven webs made from polymeric fibers and filaments. The nonwoven webs can be made from crimped polymeric fibers and filaments and/or from fibers and filaments having a shaped cross-sectional profile. For example, crimped bicomponent polyethylene/polypropylene fibers can be used. Shaped fibers include pentalobal fibers and hollow fibers.

As shown in FIG. 8, once the appropriate substrate 77 is chosen, the substrate is fed through the nip 82. In one embodiment, the point unbonded material 76 is formed through a thermal bonding process. For instance, in one embodiment, the pattern roll 78 and/or the smooth roll 80 can be heated to a temperature sufficient to melt and fuse the substrate 77 in the areas between the tufts 31. The temperature to which the rolls 78 and 80 are heated depends upon the particular application, and particularly on the materials that are used to form the substrate 77. The temperature to which the rolls are heated to also dependent upon the amount of pressure applied to the substrate 77.

Besides thermal bonding, ultrasonic bonding can also be used to produce the point unbonded material 76. Ultrasonic bonding can be carried out using a stationary device (not shown) or a rotary device as shown in FIG. 8. During ultrasonic bonding, patterned roll 78 is vibrated which causes the tufts 31 to form.

The point unbonded material 76 contains tufts having a height of at least 0.02 inches. More particularly, the height of the tufts will vary from about 0.05 inches to about 0.1 inches. As shown in FIG. 8, the tufts can have a circular shape. It should be understood, however, that tufts 31 can have any suitable shape. For instance, the tufts can be square, triangular, or even in the shape of a doughnut.

In the embodiment shown in the Figures, the tufts 31 are shown uniformly applied over one surface of the finger wipe. In other embodiments, however, the tufts may be arranged in a pattern. For example, in other embodiments, the tufts may be arranged in a circular pattern, a spiral pattern, or in any other suitable pattern. Such a pattern may assist in scrubbing an adjacent surface with the finger wipe.

The total bond area surrounding the tufts 31 can also vary depending upon the particular application. For most embodiments, the bond area surrounding the tufts can be from about 15% to about 40% of the surface area of the material, and particularly from about 20% to about 40% of the surface area of the material.

Besides point unbonded materials, there are many other methods for creating texturized surfaces on base webs and many other texturized materials can be utilized.

Examples of known nonwoven, texturized materials, include rush transfer materials, flocked materials, wireform nonwovens, and the like. Moreover, through-air bonded fibers, such as through-air bonded bicomponent spunbond, or point unbonded materials, such as point unbonded spunbond fibers, can be incorporated into the base web to provide texture to the wipe.

Textured webs having projections from about 0.1 mm to about 25 mm, such as pinform meltblown or wireform meltblown, can also be utilized in a base web of the present invention. Still another example of suitable materials for a texturized base web includes textured coform materials. In general, "coform" means a process in which at least one meltblown diehead is arranged near a chute through which other materials are added to the web while it forms. Such other materials can include, for example, pulp, superabsorbent particles, or cellulose or staple fibers. Coform processes are described in U.S. Pat. No. 4,818,464 to Lau and U.S. Pat. No. 4,100,324 to Anderson, et al. Webs produced by the coform process are generally referred to as coform materials.

In one embodiment, the texturized material can be a loop material. As used herein, a loop material refers to a material that has a surface that is at least partially covered by looped bristles. For instance, referring to FIG. 9, one embodiment of a finger wipe generally 210 is shown that incorporates a loop material. In particular, the finger wipe 210 includes a first panel 220 and a second panel 230. The second panel 230 is constructed in accordance with the present invention and includes a reservoir as described above. The second panel 230 includes a liquid impermeable layer 234 adjacent the fingers of the user and a cover layer 232 that includes looped bristles. As shown, in this embodiment, the finger wipe 210 is configured to fit around a pair of fingers 212.

The looped bristles that can be used in the present invention can vary depending upon the particular application. For instance, the stiffness of the looped bristles can be varied by varying different factors, including the height of the loop, the inherent properties of the looped material, the fiber diameter, the fiber type, and any post-formation treatments ((e.g.) chemical coatings) that may be performed on the looped material. Further, the looped bristles can be sparsely spaced apart or can be densely packed together.

The loop material can be made in a number of different ways. For example, the loop can be a woven fabric or a knitted fabric. In one embodiment, the loop material is made by needle punching loops into a substrate. In other embodiments, the loop material can be formed through a hydroentangling process or can be molded, such as through an injection molding process. Of course, any other suitable technique known in the art for producing looped bristles can also be used.

In one particular embodiment of the present invention, the loop material used in the finger wipe is a loop material commonly used in hook and loop fasteners. For example, VELCRO loops No. 002 made by VELCRO, USA, Inc. can be used. This material is made with nylon loops. In an alternative embodiment, the looped fastener material can be elastic. Elastic woven loop materials include VELSTRETCH Tape 9999 and MEDFLEX Tape 9399, both marketed by VELCRO, USA, Inc.

Liquid Impermeable Layer

In addition to a cover layer, as described above, the finger wipe may include a liquid impermeable layer that is positioned between the reservoir and the interior of the finger wipe. The liquid impermeable layer may be incorporated into only the second panel 30 or may be incorporated into both the first panel 20 and the second panel 30.

In one embodiment of the present invention, the liquid impermeable layer can be made from liquid-impermeable plastic films, such as polyethylene and polypropylene films. Generally, such plastic films are impermeable to gases and water vapor, as well as liquids.

While completely liquid-impermeable films can prevent the migration of liquid from outside the wipe to the finger, the use of such liquid- and vapor-impermeable barriers can sometimes result in a relatively uncomfortable level of humidity being maintained in the finger wipe. As such, in some embodiments, breathable, liquid-impermeable barriers are desired. As used herein, the term "breathable" means that the barrier or film is pervious to water vapor and gases. In other words, "breathable barriers" and "breathable films" allow water vapor and gases to pass therethrough, but not necessarily liquids.

For instance some suitable breathable, liquid-impermeable barriers can include barriers such as disclosed in U.S. Pat. No. 4,828,556 to Braun, et al., which is incorporated herein in its entirety by reference. The breathable barrier of Braun. et al. is a multilayered, clothlike barrier comprised of at least three layers. The first layer is a porous nonwoven web; the second layer, which is joined to one side of the first layer, comprises a continuous film of PVOH; and the third layer, which is joined to either the second layer or the other side of the first layer not joined with the second layer, comprises another porous nonwoven web. The second layer continuous film of PVOH is not microporous, meaning that it is substantially free of voids which connect the upper and lower surfaces of the film.

In other cases, various films can be constructed with micropores therein to provide breathability. The micropores form what is often referred to as tortuous pathways through the film. Liquid contacting one side of the film does not have a direct passage through the film. Instead, a network of microporous channels in the film prevents water from passing, but allows water vapor to pass.

In some instances, the breathable, liquid-impermeable barriers are made from polymer films that contain any suitable substance, such as calcium carbonate. The films are made breathable by stretching the filled films to create the microporous passageways as the polymer breaks away from the calcium carbonate during stretching. In some embodiments, the breathable film layers can be used in thicknesses of from about 0.01 mils to about 5 mils, and in other embodiments, from about 0.01 mils to about 1.0 mils.

An example of a breathable, yet fluid penetration-resistant material is described in U.S. Pat. No. 5,591,510 to Junker, et al., which is incorporated herein by reference. The fabric material described in Junker, et al. contains a breathable outer layer of paper stock and a layer of breathable, fluid-resistant nonwoven material. The fabric also includes a thermoplastic film having a plurality of perforations which allow the film to be breathable while resisting direct flow of liquid therethrough.

In addition to the films mentioned above, various other breathable films can be utilized in the present invention. One type of film that may be used is a nonporous, continuous film, which, because of its molecular structure, is capable of forming a vapor-permeable barrier. Among the various polymeric films which fall into this type include films made from a sufficient amount of poly(vinyl alcohol), polyvinyl acetate, ethylene vinyl alcohol, polyurethane, ethylene methyl acrylate, and ethylene methyl acrylic acid to make them breathable. It is believed that films made from such polymers solubilize water molecules and allow transportation of those molecules from one surface of the film to the other. Accordingly, such films may be sufficiently continuous, i.e., nonporous, to make them liquid-impermeable but still allow for vapor permeability.

Still, other breathable, liquid-impermeable barriers that can be used in the present invention are disclosed in U.S. patent application Ser. No. 08/928,787 entitled "Breathable, Liquid-Impermeable, Apertured Film/Nonwoven Laminate and Process for Making the Same", which is incorporated herein in its entirety by reference. For example, breathable films and/or apertured films can be utilized in the present invention. Such films can be made within a laminate structure. In one embodiment, a breathable, liquid-impermeable, apertured film/nonwoven laminate material can be formed from a nonwoven layer, an apertured film layer, and a breathable film layer. The layers may be arranged so that the apertured film layer or the breathable film layer is attached to the nonwoven layer.

For instance, in one embodiment, an apertured film can be used in the present invention that is made from any thermoplastic film, including polyethylene, polypropylene, copolymers of polypropylene or polyethylene, or calcium carbonate-filled films. The particular aperturing techniques utilized to obtain the apertured film layer may be varied. The film may be formed as an apertured film or may be formed as a continuous, non-apertured film and then subjected to a mechanical aperturing process.

Liquid impermeable layers, as described above, can be used alone or incorporated into a laminate when used to construct the finger wipe of the present invention. When incorporated into a laminate, the laminate can include various nonwoven webs in combination with the liquid impermeable layer. For instance, liquid impermeable laminates can be formed from many processes, such as for example, meltblowing processes, spunbonding processes, coforming processes, spunbonding/meltblowing/spunbonding processes (SMS), spunbonding/meltblowing processes (SM), and bonded carded web processes. For instance, in one embodiment, the nonwoven layer of a laminate liquid impermeable layer of the present invention is a spunbond/meltblown/spunbond (SMS) and/or spunbond/meltblown (SM) material. An SMS material is described in U.S. Pat. No. 4,041,203 to Brock. et al. which is incorporated herein in its entirety by reference. Other SMS products and processes are described for example in U.S. Pat. No. 5,464,688 to Timmons, et al., U.S. Pat. No. 5,169,706 to Collier, et al. and U.S. Pat. No. 4,766,029 to Brock. et al., all of which are also incorporated herein in their entireties by reference. Generally, an SMS material will contain a meltblown web sandwiched between two exterior spunbond webs. Such SMS laminates are available from Kimberly-Clark Corporation under marks such as Spunguard® and Evolution®. The spunbonded layers on the SMS laminates provide durability and the internal meltblown barrier layer provides porosity and additional clothlike feel. Similar to an SMS laminate, an SM laminate is a spunbond layer laminated to a meltblown layer.

In forming a finger wipe of the present invention with a liquid impermeable layer, the layer can be bonded together with the other layers of the wipe in a number of various ways. Thermal bonding, adhesive bonding, ultrasonic bonding, extrusion coating, and the like, are merely examples of various bonding techniques that may be utilized in the present process to attach the liquid impermeable layer to the fibrous layers of the finger wipe.

In some embodiments, any of the above layers and/or materials can also be dyed or colored so as to form a base web or liquid impermeable layer having a particular color. For example, in one embodiment, the liquid impermeable layer can be provided with a colored background.

Elastic Component

As described above, the finger wipe 10 may include one or more elastic components for providing the wipe with form-fitting properties. In one particular embodiment, for instance, the finger wipe 10 may include a first panel 20 made from an elastic material. In one embodiment, for instance, the first panel 20 can contain elastic strands or sections uniformly or randomly distributed throughout the material. Alternatively, the elastic component can be an elastic film or an elastic nonwoven web.

In general, any material known in the art to possess elastomeric characteristics can be used in the present invention as an elastomeric component. Useful elastomeric materials can include, but are not limited to, films, foams, nonwoven materials, etc. For example, suitable elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers for the A and A' blocks, and the present block copolymers are intended to embrace linear, branched and radial block copolymers. In this regard, the radial block copolymers may be designated (A-B)m-X, wherein X is a polyfunctional atom or molecule and in which each (A-B)m- radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer," and particularly "A-B-A" and "A-B" block copolymer, is intended to embrace all block copolymers having such rubbery blocks and thermoplastic blocks as discussed above, which can be extruded (e.g., by meltblowing), and without limitation as to the number of blocks. The elastomeric nonwoven web may be formed from, for example, elastomeric (polystyrene/poly(ethylene-butylene)/polystyrene) block copolymers. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220; 4,323,534; 4,834,738; 5,093,422; and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor. et al. In such polymers, A is a thermoplastic polymer block and B is an isoprene monomer unit hydrogenated to substantially a poly(ethylene-propylene) monomer unit. An example of such a tetrablock copolymer is a styrene-poly(ethylene-propylene)-styrene-poly(ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B.F. Goodrich & Co. or MORTHANE® from Morton Thiokol Corp., polyester elastomeric materials such as, for example, those available under the trade designation HYTREL® from E.I. DuPont De Nemours & Company, and those known as ARNITEL®, formerly available from Akzo Plastics of Amhem, Holland and now available from DSM of Sittard, Holland.

Another suitable material is a polyester block amide copolymer. Elastomeric polymers can also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. No. 4,803,117.

When incorporating an elastomeric component, such as described above, into a base web of the present invention, it is often desired that the elastomeric material form an elastic laminate with one or more other layers, such as foams, films, apertured films, and/or nonwoven webs. The elastic laminate generally contains layers that can be bonded together so that at least one of the layers has the characteristics of an elastic polymer. Examples of elastic laminates include, but are not limited to, stretch-bonded laminates and neck-bonded laminates.

The elastic member used in neck-bonded materials, stretch-bonded materials, stretch-bonded laminates, neck-bonded laminates and in other similar laminates can be made from materials, such as described above, that are formed into films, such as a microporous film, fibrous webs, such as a web made from meltblown fibers, spunbond filaments or foams. A film, for example, can be formed by extruding a filled elastomeric polymer and subsequently stretching it to render it microporous.

In one embodiment, the elastic member can be a neck stretched bonded laminate. As used herein, a neck stretched bonded laminate is defined as a laminate made from the combination of a neck-bonded laminate and a stretch-bonded laminate. Examples of necked stretched bonded laminates are disclosed in U.S. Pat. Nos. 5,114,781 and 5,116,662, which are both incorporated herein by reference. Of particular advantage, a neck stretch bonded laminate is stretchable in the machine direction and in a cross machine direction. Further, a neck stretch-bonded laminate can be made with a nonwoven basing that is texturized. In particular, the neck stretched bonded laminate can be made so as to include a nonwoven facing that gathers and becomes bunched so as to form a textured surface. In this manner, the neck stretched bonded laminate can be used to form the entire finger wipe having stretch characteristics in two directions and having a textured surface for cleaning the teeth and gums of a user.

Figure 10:
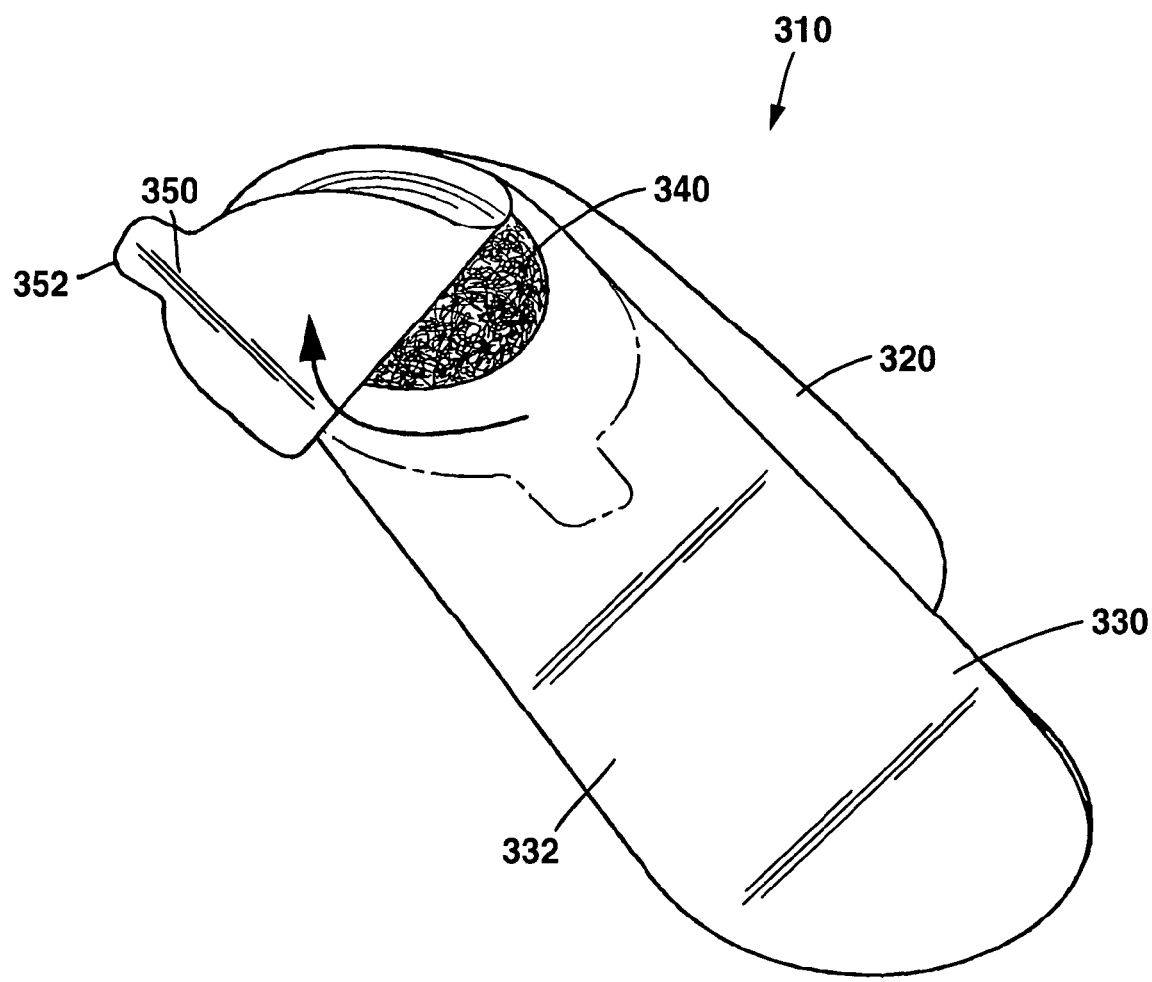
FIG. 10 is a perspective view of another embodiment of a finger wipe made according to the present invention.

Referring to FIG. 10, another embodiment of a finger wipe generally 310 made in accordance with the present invention is illustrated. In this embodiment, the finger wipe 310 includes a first panel 320 attached to a second panel 330. It should be understood, however, that the finger wipe 310 may also be made from a single unitary piece. In the embodiment illustrated in FIG. 10, the first panel 320 may include an elastic component for providing the finger wipe with form-fitting properties.

The second panel 330 includes a liquid impermeable layer 332. Attached to the liquid impermeable layer 332 is a retention material 340. The retention material 340 may be, for instance, any suitable material capable of retaining the composition, whether the composition is a liquid or a solid, until the finger wipe is placed into use. The retention material 340, for instance, may comprise a porous material such as a fibrous material, a foam material, and the like. When a fibrous material is used, for example, the fibrous material may comprise a batt of fibers or may comprise a fabric material, such as woven, nonwoven, or knitted material. As shown in FIG. 10, the retention material 340 is positioned generally in the fingertip area of the finger wipe 310. In other embodiments, however, the retention material 340 may be positioned at other locations or may have a larger or smaller size. The retention material 340 may be bonded to the liquid impermeable layer 332 using any suitable bonding method.

In accordance with the present invention, the retention material 340 is treated with or impregnated with a composition, such as a liquid or a solid. The composition, for example, may be any of the compositions described above.

In order to protect the composition contained in the retention material 340 prior to use of the finger wipe 310, the finger wipe further includes a release layer 350 which covers the retention material 340. As shown in FIG. 10, the release layer 350 may include a tab 352 which may be pulled upon by a user in order to remove the release layer.

The release layer 350 can be made from any suitable material capable of protecting and containing the composition within the retention material 340. The release layer 350, for instance, may comprise a film or a coated paper, such as a wax or silicone paper.

The release layer 350 may be attached to the finger wipe 310 using any suitable releasable bonding method. For example, in one embodiment, an adhesive material, such as a pressure sensitive adhesive may attach the release layer to the finger wipe at locations that surround the retention material 340. In other embodiments, the release layer 350 may be thermally or ultrasonically bonded to the finger wipe in a releasable manner.

Figure 11:
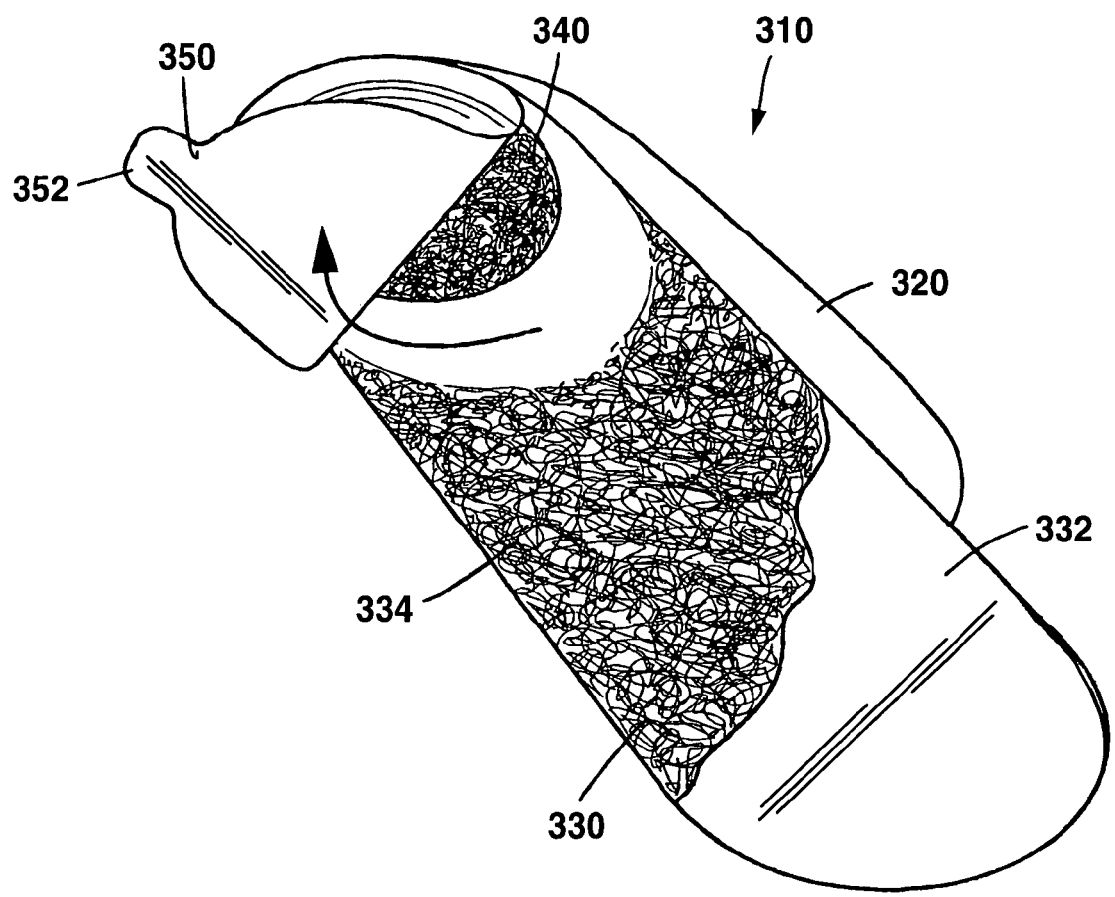
FIG. 11 is a perspective view of still another embodiment of a finger wipe made according to the present invention.

Referring to FIG. 11, still another embodiment of a finger wipe generally 310 made in accordance with the present invention is shown. Like reference numerals similar to FIG. 10 have been used in FIG. 11 to represent similar elements.

As shown in FIG. 11, the finger wipe 310 includes a first panel 320 attached to a second panel 330. The second panel 330 includes a liquid impermeable layer 332, a retention material 340 that is impregnated with a composition and a release layer 350. In this embodiment, the finger wipe 310 further includes a cover layer 334 which surrounds the retention material 340 and covers the remainder of the finger wipe. The cover layer 334 may be made from any of the materials described above with respect to the cover layer illustrated in FIGS. 1-6. The cover layer 334 may be added to the finger wipe 310 in order to provide greater amounts of a liquid absorbent material, to provide a scrubbing surface, or for any other suitable purpose.

The dimensions of finger wipes that are formed in accordance with the present invention will depend upon the particular application and purpose for which the finger wipe is to be used. For instance, the finger wipe can be constructed in order to fit around the finger of an adult or the finger of a child. Further, the finger wipe can also be constructed to fit around two fingers. For most single finger wipes, the wipe should have a length of from about 1 inch to about 7 inches and a median flattened width of from about 0.5 inches to about 4 inches. When constructed to fit around two fingers, the finger wipe can have a median width of from about 0.75 inches to about 2.5 inches, depending on the elasticity of the wipe.

Prior to being shipped and sold, the finger wipe of the present invention can be placed in various packaging, if desired. Various packaging materials that can be used include ethylene vinyl alcohol (EVA) films, film foil laminates, metalized films, multi-layered plastic films, and the like.

Although various embodiments of the invention have been described using specific terms, devices, and methods, such description is for illustrative purposes only. The words used are words of description rather than of limitation. It is to be understood that changes and variations may be made by those of ordinary skill in the art without departing from the spirit or scope of the present invention, which is set forth in the following claims. In addition, it should be understood that aspects of the various embodiments may be interchanged both in whole or in part. Therefore, the spirit and scope of the appended claims should not be limited to the description of the preferred versions contained therein.

What is claimed:

1. A finger wipe comprising a hollow member having an open end and a closed end located opposite the open end, the hollow member having a shape configured for the insertion of no more than two fingers, the hollow member further comprising:
   a liquid impermeable layer positioned to prevent liquids from contacting a finger contained in the hollow member;
   a cover layer including at least one liquid permeable portion, wherein the cover layer comprises a material selected from the group consisting of spunbonded webs, meltblown webs, spunbonded/meltblown/spunbonded webs, spunbonded/meltblown webs, coform webs, and bonded carded webs;
   a reservoir positioned in between the liquid impermeable layer and the cover layer, the reservoir being configured to be ruptured by a user; and
   a liquid composition contained in the reservoir, wherein, when the reservoir is ruptured by a user, the liquid composition is released from the reservoir and migrates through the liquid permeable portion of the cover layer.

2. A finger wipe as defined in claim 1, wherein the liquid impermeable layer comprises a film.

3. A finger wipe as defined in claim 1, wherein the cover layer comprises a nonwoven material.

4. A finger wipe as defined in claim 1, wherein the cover layer comprises a perforated fabric layer.

5. A finger wipe as defined in claim 1, wherein the reservoir is constructed from a film, the film forming a rupturable bladder for holding the composition.

6. A finger wipe as defined in claim 5, wherein the reservoir is attached to the liquid impermeable layer.

7. A finger wipe as defined in claim 1, wherein the reservoir is constructed so as to rupture when squeezed between a user's pair of opposing fingers.

8. A finger wipe as defined in claim 1, wherein the hollow member comprises a first panel attached to a second panel along a seam, the first panel comprising an elastic member, the second panel comprising the liquid impermeable layer, the cover layer, and the reservoir.

9. A finger wipe as defined in claim 1, further containing an elastic component for providing the finger wipe with form-fitting properties.

10. A finger wipe as defined in claim 9, wherein the elastic component comprises an elastic nonwoven material.

11. A finger wipe as defined in claim 1, wherein the composition consists essentially of a liquid.

12. A finger wipe as defined in claim 1, further comprising a second reservoir in fluid communication with the first reservoir, the second reservoir also containing the composition for providing further amounts of the composition to the first reservoir.

13. A finger wipe as defined in claim 1, wherein the entire cover layer is liquid permeable.

14. A finger wipe as defined in claim 1, wherein the liquid permeable portion of the cover layer has a basis weight that is less than the basis weight of the remainder of the cover layer.

15. A finger wipe as defined in claim 1, wherein the hollow member comprises a first panel and a second panel, the first panel and the second panel being sealed together to form a seam, the second panel comprising the liquid impermeable layer, the cover layer, and the reservoir, the first panel and the second panel including an overlapping portion that extends beyond the seam, the overlapping portion having a width of at least about 0.25 inches, the overlapping portion being periodically severed along the width of the overlapping portion.

16. A finger wipe as defined in claim 1, wherein the composition contained in the reservoir comprises a cleaning solution or a pharmaceutical.

17. A finger wipe as defined in claim 1, wherein the composition contained in the reservoir comprises a tooth cleaner.

18. A finger wipe as defined in claim 1, wherein the composition contained within the reservoir comprises a mite control agent, a tick control agent, or a flea control agent.

19. A finger wipe as defined in claim 1, wherein the cover layer includes a texturized surface.

20. A finger wipe as defined in claim 19, wherein the texturized surface comprises looped bristles or a point unbonded material.

21. A finger wipe as defined in claim 1, wherein the reservoir is positioned directly against the cover layer opposite the at least one liquid permeable portion.

22. A finger wipe comprising a hollow member having an open end and a closed end located opposite the open end, the hollow member having a shape configured for the insertion of no more than two fingers, the hollow member comprising a first panel attached to a second panel along a seam, the first panel comprising an elastic member for providing the finger wipe with form-fitting properties, the second panel comprising:
   a liquid impermeable layer positioned to prevent liquids from contacting a finger contained in the hollow member;
   a cover layer including at least one liquid permeable portion;
   a reservoir positioned in between the liquid impermeable layer and the cover layer, the reservoir being configured to be ruptured by a user; and
   a liquid composition contained in the reservoir, wherein, when the reservoir is ruptured by a user, the liquid composition is released from the reservoir and migrates through the liquid permeable portion of the cover layer.

23. A finger wipe as defined in claim 22, wherein the liquid impermeable layer comprises a film.

24. A finger wipe as defined in claim 23, wherein the cover layer comprises a nonwoven material.

25. A finger wipe as defined in claim 24, wherein the reservoir is constructed from a film, the film forming a rupturable bladder for holding the composition.

26. A finger wipe as defined in claim 22, wherein the elastic member comprises a neck-bonded laminate or a stretch-bonded laminate.

27. A finger wipe as defined in claim 22, wherein the composition contained in the reservoir comprises a cleaning solution or a pharmaceutical.

28. A finger wipe as defined in claim 22, wherein the composition contained in the reservoir comprises a tooth cleaner.

29. A finger wipe as defined in claim 22, wherein the composition contained within the reservoir comprises a mite control agent, a tick control agent, or a flea control agent.

30. A finger wipe as defined in claim 22, wherein the cover layer comprises a material selected from the group consisting of spunbonded webs, meltblown webs, spunbonded/meltblown/spunbonded webs, spunbonded/meltblown webs, coform webs, and bonded carded webs.

31. A finger wipe as defined in claim 22, wherein the first panel and the second panel including an overlapping flange portion that extends beyond the seam, the overlapping portion having a width of at least about 0.25 inches, the overlapping portion being periodically severed along the width of the overlapping portion.

32. A finger wipe as defined in claim 22, wherein the reservoir is positioned directly against the cover layer opposite the at least one liquid permeable portion.

33. A finger wipe comprising a hollow member having an open end and a closed end located opposite the open end, the hollow member having a shape configured for the insertion of no more than two fingers, the hollow member further comprising:
   a liquid impermeable layer positioned to prevent liquids from contacting a finger contained in the hollow member;
   a cover layer including at least one liquid permeable portion, the liquid permeable portion of the cover layer having a basis weight that is less than the basis weight of the remainder of the cover layer;
   a reservoir positioned in between the liquid impermeable layer and the cover layer, the reservoir being configured to be ruptured by a user; and
   a liquid composition contained in the reservoir, wherein, when the reservoir is ruptured by a user, the liquid composition is released from the reservoir and migrates through the liquid permeable portion of the cover layer.

34. A finger wipe comprising a hollow member having an open end and a closed end located opposite the open end, the hollow member having a shape configured for the insertion of no more than two fingers, the hollow member further comprising:
   a liquid impermeable layer positioned to prevent liquids from contacting a finger contained in the hollow member;
   a cover layer including at least one liquid permeable portion;
   a reservoir positioned in between the liquid impermeable layer and the cover layer, the reservoir being configured to be ruptured by a user; and
   a liquid composition contained in the reservoir, wherein, when the reservoir is ruptured by a user, the liquid composition is released from the reservoir and migrates through the liquid permeable portion of the cover layer, wherein the composition contained within the reservoir comprises a mite control agent, a tick control agent, or a flea control agent.

35. A finger wipe comprising a hollow member having an open end and a closed end located opposite the open end, the hollow member having a shape configured for the insertion of no more than two fingers, the hollow member further comprising:
   a liquid impermeable layer positioned to prevent liquids from contacting a finger contained in the hollow member;

a cover layer including at least one liquid permeable portion, the cover layer including a texturized surface comprising looped bristles or a point unbonded material;
a reservoir positioned in between the liquid impermeable layer and the cover layer, the reservoir being configured to be ruptured by a user; and
a liquid composition contained in the reservoir, wherein, when the reservoir is ruptured by a user, the liquid composition is released from the reservoir and migrates through the liquid permeable portion of the cover layer.

* * * * *